US006391574B1

(12) United States Patent
Rine et al.

(10) Patent No.: US 6,391,574 B1
(45) Date of Patent: May 21, 2002

(54) AFC1 AND RCE1: ISOPRENYLATED CAAX PROCESSING ENZYMES

(75) Inventors: Jasper D. Rine, Moraga; Victor L. Boyartchuk, Berkeley; Matthew N. Ashby, Mill Valley, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/184,964

(22) Filed: Nov. 3, 1998

Related U.S. Application Data

(63) Continuation of application No. 08/902,774, filed on Jul. 30, 1997, now abandoned.
(60) Provisional application No. 60/023,491, filed on Aug. 7, 1996.

(51) Int. Cl.$^7$ .............................. C12Q 1/37; C12N 9/50; C12N 1/20; C12N 15/52; C12N 5/00

(52) U.S. Cl. ..................... 435/23; 435/219; 435/252.3; 435/320.1; 435/325; 435/471; 435/6; 536/23.2

(58) Field of Search ....................... 435/6, 4, 24, 252.2, 435/320.1, 325; 536/23.2

(56) References Cited

PUBLICATIONS

Akopyan, T.N., et al., Cleavage of farnesylated COOH–terminal heptapeptide of mouse N–ras by brain microsomal membranes: evidence for a carboxypeptidase which specifically removes the COOH–terminal methionine. Biochem Biophys Res Commun, 1992. 187(3):p. 1336–42.

Akopyan, T.N., et al., Proteolytic processing of farnesylated peptides: assay and partial purification from pig brain membranes of an endopeptidase which has the characteristics of E.C. 3.4.24.15. Biochem Biophys Res Commun, 1994. 198(2):p. 787–94.

Ashby, M.N., D.S. King, and J. Rine, Endoproteolytic processing of a farnesylated peptide in vitro. Proc Natl Acad Sci U S A, 1992. 89(10):p. 4613–7.

Ashby, M.N., et al., Isolation and DNA sequence of the STE14 gene encoding farnesyl cysteine: carboxyl methyltransferase. Yeast, 1993. 9(8):p. 907–13.

Ashby, M.N. and J. Rine, Ras and a–factor converting enzyme. Methods Enzymol, 1995. 250:p. 235–51.

Ashby, M.N., CaaX converting enzymes. Curr Opin Lipidol, 1998. 9(2):p. 99–102.

Auffray, C., et al., GenBank Accession No. Z43273, Nov. 11, 1994.

Boyartchuk, V.L., M.N. Ashby, and J. Rine, Modulation of Ras and a–factor function by carboxyl–terminal proteolysis [see comments]. Science, 1997. 275(5307):p. 1796–800.

Chen, Y., Y.T. Ma, and R.R. Rando, Solubilization, partial purification, and affinity labeling of the membrane–bound isoprenylated protein endoprotease. Biochemistry, 1996. 35(10):p. 3227–37.

Ding, J., et al., Farnesyl–L–cysteine analogs can inhibit or initiate superoxide release by human neutrophils. J Biol Chem, 1994. 269(24):p. 16837–44.

Dudler, T. and M.H. Gelb, Replacement of the H–Ras farnesyl group by lipid analogues: implications for downstream processing and effector activation in Xenopus oocytes. Biochemistry, 1997. 36(41):p. 12434–41.

Farh, L., D.A. Mitchell, and R.J. Deschenes, Farnesylation and proteolysis are sequential, but distinct steps in the CaaX box modification pathway. Arch Biochem Biophys, 1995. 318(1):p. 113–21.

Fujimura–Kamada, K., F.J. Nouvet, and S. Michaelis, A novel membrane–associated metalloprotease, Ste24p, is required for the first step of NH2–terminal processing of the yeast a–factor precursor. J Cell Biol, 1997. 136(2):p. 271–85.

Georgopapadakou, N.H., et al., A radiometric assay for Ras–processing peptidase using an enzymatically radiolabeled peptide. Anal Biochem, 1994. 218(2):p. 273–7.

Giner, J.L. and R.R. Rando, Novel methyltransferase activity modifying the carboxy terminal bis(geranylgeranyl)–Cys–Ala–Cys structure of small GTP–binding proteins. Biochemistry, 1994. 33(50):p. 15116–23.

Gutierrez, L., et al., Post–translational processing of p21ras is two–step and involves carboxyl–methylation and carboxy–terminal proteolysis. Embo J, 1989. 8(4):p. 1093–8.

Hancock, J.F., K. Cadwallader, and C.J. Marshall, Methylation and proteolysis are essential for efficient membrane binding of prenylated p21K–ras(B). Embo J, 1991. 10(3):p. 641–6.

Hancock, J.F., Reticulocyte lysate assay for in vitro translation and posttranslational modification of Ras proteins. Methods Enzymol, 1995. 225:p. 60–5.

Hiwasa, T., T. Sawada, and S. Sakiyama, Synergistic induction of anchorage–independent growth of NIH3T3 mouse fibroblasts by cysteine proteinase inhibitors and a tumor promoter. J Biol Chem, 1996. 271(16):p. 9181–4.

Hrycyna, C.A. and S. Clarke, Maturation of isoprenylated proteins in *Saccharomyces cerevisiae*. Multiple activities catalyze the cleavage of the three carboxyl– terminal amino acids from farnesylated substrates in vitro. J Biol Chem, 1992. 267(15):p. 10457–64.

(List continued on next page.)

Primary Examiner—Ponnathapu Achutamurthy
(74) Attorney, Agent, or Firm—Richard Aron Osman

(57) ABSTRACT

Two genes which encode polypeptides that mediate post-prenylation processing steps in CAAX polypeptides such as Ras are provided. The two genes (AFC1 and RCE1) encode polypeptides that mediate the removal of the AAX tripeptide from the CAAX polypeptide following prenylation. The genes and encoded polypeptides provide assays for testing compounds for an effect on post-prenylation processing steps. A heat shock assay for assessing Ras activity is also provided.

23 Claims, No Drawings

PUBLICATIONS

Hrycyna, C.A. and S. Clarke, Purification and characterization of a novel metalloendopeptidase from *Saccharomyces cerevisiae*. Biochemistry, 1993. 32(42):p. 11293–301.

Jang, G.F., K. Yokoyama, and M.H. Gelb, A prenylated protein-specific endoprotease in rat liver microsomes that produces a carboxyl-terminal tripeptide. Biochemistry, 1993. 32(36):p. 9500–7.

Jang, G.F. and M.H. Gelb, Substrate specificity of mammalian prenyl protein-specific endoprotease activity [published erratum appears in Biochemistry Apr. 14, 1998; 37(15):5336]. Biochemistry, 1998. 37(13):p. 4473–81.

Kato, K., et al., Isoprenoid addition to Ras protein is the critical modification for its membrane association and transforming activity. Proc Natl Acad Sci U S A, 1992. 89(14):p. 6403–7.

Ma, Y.T., A. Chaudhuri, and R.R. Rando, Substrate specificity of the isoprenylated protein endoprotease. Biochemistry, 1992. 31(47):p. 11772–7.

Ma, Y.T. and R.R. Rando, A microsomal endoprotease that specifically cleaves isoprenylated peptides. Proc Natl Acad Sci U S A, 1992. 89(14):p. 6275–9.

Ma, Y.T., B.A. Gilbert, and R.R. Rando, Inhibitors of the isoprenylated protein endoprotease [published erratum appears in Biochemistry Jun. 8, 1993; 32(22):5924]. Biochemistry, 1993. 32(9):p. 2386–93.

Ma, Y.T. and R.R. Rando, Endoproteolysis of non-CAAX-containing isoprenylated peptides. FEBS Lett, 1993. 332(1–2):p. 105–10.

Ma, Y.T., et al., Mechanistic studies on human platelet isoprenylated protein methyltransferase: farnesylcysteine analogs block platelet aggregation without inhibiting the methyltransferase. Biochemistry, 1994. 33(18):p. 5414–20.

Marra, M., et al., GenBank Accession No. W14344, Sep. 10, 1996.

Nishii, W., et al., Partial purification and characterization of a CAAX-motif-specific protease from bovine brain using a novel fluorometric assay. J Biochem (Tokyo), 1997. 122(2):p. 402–8.

Parish, C.A., D.P. Brazil, and R.R. Rando, On the mechanism of the inhibition of transducin function by farnesylcysteine analogs. Biochemistry, 1997. 36(9):p. 2686–93.

Perez–Sala, D., et al., Analogs of farnesylcysteine induce apoptosis in HL-60 cells. FEBS Lett, 1998. 426(3):p. 319–24.

Powers, S., et al., "RAM, a Gene of Yeast Required for a Functional Modification of RAS Proteins and for Production of Mating Pheromone a-Factor," Cell, 1986, 47:413–422.

Rando, R.R. and Y.T. Ma, Isoprenylated protein endopeptidase. Methods Enzymol, 1994. 244:p. 632–9.

Schmidt, W.K., et al., Endoplasmic reticulum membrane localization of rce1p and ste24p, yeast proteases involved in carboxyl-terminal CAAX protein processing and amino-terminal a-factor cleavage [In Process Citation]. Proc Natl Acad Sci U S A, 1998. 95(19):p. 11175–80.

Shi, Y.Q. and R.R. Rando, Kinetic mechanism of isoprenylated protein methyltransferase. J Biol Chem, 1992. 267(14):p. 9547–51.

Tam, A., et al., Dual roles for Ste24p in yeast a-factor maturation: NH2-terminal proteolysis and COOH-terminal CAAX processing. J Cell Biol, 1998. 142(3):p. 635–49.

Tan, E.W. and R.R. Rando, Identification of an isoprenylated cysteine methyl ester hydrolase activity in bovine rod outer segment membranes. Biochemistry, 1992. 31(24):p. 5572–8.

Fujiyama, A., et al., A novel yeast mutant defective in the processing of ras proteins: assessment of the effect of the mutation on processing steps, EMBO J., vol. 6, No. 1, p. 223–228 1986.

Sass, P., et al., Cloning and characterization of the high-affinity cAMP phosphodiesterase of *S. cerevisiae*, PNAS USA, 1986, 83:9303–9307.

AFC1 AND RCE1: ISOPRENYLATED CAAX PROCESSING ENZYMES

CROSS-REFERENCE TO RELATED APPLICATIONS

This application is a continuation of U.S. application Ser. No. 08/902,774 filed Jul. 30, 1997, now abandoned, which claims benefit of U.S. provisional application Ser. No. 60/023,491, filed Aug. 7, 1996.

STATEMENT OF GOVERNMENT INTEREST

This invention was made with support pursuant to Grant (Contract) No. GM 35827 awarded by the National Institutes of Health and with support pursuant to Grant (Contract) Nos. 4FT-0083 and 1RT-0026 awarded by the Tobacco-Related Disease Research Program.

BACKGROUND OF THE INVENTION

A cell possesses thousands of unique proteins that serve structural, enzymatic or signaling functions. The intracellular environment is composed of a myriad of structures and membrane-enclosed compartments. The correct subcellular localization is critical for the proper functioning of many proteins. Proteins situated at the lipid bilayer membrane are classified as peripheral proteins, whereas proteins situated within the lipid bilayer membrane are classified as integral membrane proteins. Integral membrane proteins possess intrinsic hydrophobic regions which are inserted into the lipid bilayer as they are synthesized. Typically, peripheral membrane proteins are less tightly associated with membranes and are localized to the lipid bilayer by protein-protein interactions, by intrinsic hydrophobic properties or by the post-translational addition of a lipid group.

A major class of peripheral membrane proteins, known as prenylated proteins, are modified by isoprenoids on a so-called $CAaa_1Aaa_2Xaa$ (CAAX) motif, wherein C is cysteine, $Aaa_1$ and $Aaa_2$ are aliphatic amino acids and $Xaa$ is any amino acid. This tetra-peptide sequence is located at the proteins' carboxyl termini and triggers a series of modification reactions. Of the approximately 30 known CAAX-containing proteins, the Ras family of small GTP-binding proteins are major constituents. Ras proteins localize at the inner surface of the plasma membrane where they function as key components of various signal transduction pathways or participate in cytoskeletal organization and establishment of cell polarity. The critical role of the Ras proto-oncogene in controlling cell division is exemplified by the participation of mutated forms of the Ras protein in a variety of human tumors, including colorectal carcinoma, exocrine pancreatic carcinoma and myeloid leukemias. Forms of Ras in cancer cells have mutations that distinguish the protein from Ras in normal cells.

The presence of the $CAaa_1Aaa_2Xaa$ motif sequence targets the protein for at least 3 post-translational modifications. Generally, such modifications include prenylation of the cysteine amino acid, proteolytic removal of the terminal three amino acids (i.e., the $Aaa_1Aaa_2Xaa$ tripeptide) and methylesterification of the prenylated cysteine, i.e., the C-terminus. More particularly, in the first step, a 15 carbon farnesyl or a 20 carbon geranylgeranyl isoprenyl lipid is added to the cysteine residue. The lipid which is added depends upon the amino acid at the "X" position. Following prenylation, the terminal tripeptide, i.e., the $Aaa_1Aaa_2Xaa$ tripeptide, is removed by a membrane-bound endoprotease. Thereafter, the resulting C-terminal isoprenylated cysteine is methylesterified.

It has been determined that prenylation of the CAAX motif is essential for the proper functioning of every prenylated protein that has been tested to date. However, the functional requirement of CAAX proteolysis has not been rigorously evaluated because the gene encoding the protease has been elusive. This is true despite the fact that the entire yeast genome has been sequenced and the sequences deposited in GenBank. Unfortunately, elucidation of the complete yeast genome in the absence of functional information for each yeast gene is insufficient for identification of any particular gene. Although many open reading frames (ORFs) have been identified, it is not known whether these ORFs encode functional mRNAs.

Kato, et al. (*Proc. Natl. Acad. Sci. USA*, 89:9554–9558 (1992)) monitored foci formation of NIH3T3 cells transformed with activated forms of Ras with altered CAAX sequences. They found that one sequence, CVYS, when substituted for the normal Ras CAAX sequence appeared not to have undergone proteolysis and resulted in approximately 50% reduction in foci formation. Unfortunately, the design of this experiment was not ideal because it relied on the heterologous expression of Ras from an SV40 promoter, which resulted in a considerably higher expression level than the physiological Ras promoter. Moreover, the CAAX sequence CVYS displayed a prenylation defect.

In view of the foregoing, there remains a need in the art for the identification of the genes encoding the polypeptides that participate in the post-prenylation modification reactions so that the functional importance of such enzymes can be elucidated.

SUMMARY OF THE INVENTION

The present invention includes the discovery of two families of genes which encode polypeptides that mediate the proteolytic removal of an AAX tripeptide from a prenylated CAAX protein in a cell. In yeast, the families of genes are represented by the genes AFC1 and RCE1 which encode the polypeptides Afc1p and Rce1p, respectively.

Accordingly, the invention provides vectors that includes a nucleic acid sequence which encodes an Afc1p or Rce1p polypeptide (or both polypeptides), or conservatively modified variations of Afc1p or Rce1p. Exemplar nucleic acids which encode Afc1p, or Rce1p include those set forth in SEQ ID NO:1 and SEQ ID NO:2. Recombinant cells, including recombinant yeast cells, which comprise a vector nucleic acid of the invention are also provided.

In one class of embodiments, the vector of the invention provides a nucleic acid sequence which hybridizes under stringent conditions to a nucleic acid selected from the group consisting of the AFC1, and RCE1 genes. Exemplar nucleic acids with the desired hybridization properties include those represented by the sequences of SEQ ID NO:1 and SEQ ID NO:3.

The invention provides isolated polypeptides, such as Afc1p and Rce1p, encoded by the vectors of the invention. Exemplar polypeptides include those represented by SEQ ID NO:2 and SEQ ID NO:4. Antibodies which specifically bind to the polypeptides of the invention are also provided.

In addition to nucleic acids, cells, polypeptides and antibodies, a variety of useful methods and assays are provided by the present invention. In one embodiment, the invention provides methods for inhibiting the proteolytic removal of an AAX tripeptide from a prenylated CAAX protein in a cell. Exemplar prenylated CAAX proteins include the Ras protein, a-factor, and the γ-subunit of the heterotrimeric G-protein. In these methods, a mutation is introduced into an AFC1 and/or RCE1 gene.

In one class of embodiments, the invention provides methods for inhibiting the proteolytic removal of an AAX tripeptide from a prenylated CAAX protein in a cell. In this class of embodiments, the activity of the Afc1p or Rce1p protein is blocked using an inhibitor. Exemplar inhibitors include 1,10-phenanthroline and NME 181.

The invention provides assays for testing the inhibitory activity of a potential inhibitor of the Afc1p or Rce1p proteases, which are responsible for the proteolytic removal of an AAX tripeptide of a CAAX protein in a cell. In the assay method, a test compound to be tested for inhibitory activity is provided. The test compound is contacted to a cell expressing either the AFC1 or RCE1 genes, or both. The transcriptional or translational activity of the genes or, alternatively, the activity of the encoded proteins, is measured, and typically compared to a reference, such as a control assay which establishes the activity of the measured activity in the absence of the test compound. One convenient activity which is mediated by the AFC1 and RCE1 genes is heat shock sensitivity of cells. Accordingly, in one embodiment, the measured activity is heat shock sensitivity. In a second convenient assay, the level of Afc1p or Rce1p protein in a population of cells is measured in a standard immunological assay, such as an ELISA.

In addition, the present invention provides an improved method for monitoring heat shock sensitivity, particularly in yeast, is provided. In this method, a plurality of aliquoted yeast strains in liquid are provided. Each strain is separated into a test population of cells and a control population of cells. The test population of cells is heated to a heat shock temperature of between about 40° C. and about 60° C. for a time period of between about 30 seconds and about 10 minutes, followed by cooling to a temperature of between about 0° C. and about 35° C. In a preferred embodiment, the test population of cells is heated and cooled in a PCR thermocycler to allow for better temperature control. The test population of cells and the control population of cells are grown on growth media and quantitated. The number of test and control cells are compared. The comparison of the number of cells in the test population and the control population provides a measure of heat shock sensitivity. Exemplar yeast strains include Δafc1, Δrce1, and the double deletion strain Δafc1-Δrce1.

DEFINITIONS

Unless defined otherwise, all technical and scientific terms used herein have the same meaning as commonly understood by one of ordinary skill in the art to which this invention belongs. Singleton et al. (1994) *Dictionary of Microbiology and Molecular Biology,* second edition, John Wiley and Sons (New York); Walker (ed) (1988) The *Cambridge Dictionary of Science and Technology,* The press syndicate of the University of Cambridge, NY; and Hale and Marham (1991) The Harper Collins Dictionary of Biology Harper Perennial, NY provide one of skill with a general dictionary of many of the terms used in reference to this invention. Although any methods and materials similar or equivalent to those described herein can be used in the practice or testing of the present invention, certain preferred methods and materials are described in detail. For purposes of the present invention, the following terms are defined below.

"$CAaa_1Aaa_2Xaa$" or, interchangeably, "CAAX," as used herein, refers to a carboxy-terminal motif sequence, wherein C is cysteine, $Aaa_1$ and $Aaa_2$ are aliphatic amino acids and Xaa is any one of a number of different amino acids. The presence of the $CAaa_1Aaa_2Xaa$ motif sequence targets the protein for at least 3 post-translational modifications. Such modifications include prenylation of the cysteine amino acid, proteolytic removal of the terminal three amino acids (i.e., the $Aaa_1Aaa_2Xaa$ tripeptide) and methylesterification of the prenylated cysteine, i.e., the C-terminus. Examples of CAAX-containing proteins include, but are not limited to, fungal mating pheromones, RAS proteins, nuclear lamins and the γ-subunit of trimeric G-proteins (see, e.g., Hrycyna, et al., *EMBO Journal,* 10(7):1699–1709 (1991)).

An "$Aaa_1Aaa_2Xaa$ tripeptide," as used herein refers to the terminal three amino acids of the $CAaa_1Aaa_2Xaa$ motif sequence.

A "prenylated $CAaa_1Aaa_2Xaa$ protein" refers to a protein containing a $CAaa_1Aaa_2Xaa$ motif sequence, wherein the cysteine amino acid has been prenylated by the addition of a geranyl, farnesyl or geranylgeranyl lipid.

"Proteolytic cleavage," as used herein, refers to the removal of the terminal three amino acids of the $CAaa_1Aaa_2Xaa$ motif sequence through the cleavage of a peptide bond by a protease.

"Inhibit" or, interchangeably, "antagonize," or "blocking the activity" as used herein, refers to the reduction or prevention of a reaction or process.

A "yeast strain" is a population of yeast cells, each of which share a particular phenotype or a particular genotype.

A "test population of cells" is a population of cells to be characterized, e.g., in a method or an assay. A "control" population of cells is a population of cells which are used to determine that an observed effect in a method or assay is the result of experimental manipulation, and not the result of an unknown or unintended environmental parameter.

A "vector" is a composition which can transduce, transfect, transform or infect a cell, thereby causing the cell to replicate or express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell, nor that any particular cell type is the subject of transduction. A cell is "transformed" by a nucleic acid when the nucleic acid is transduced into the cell and stably replicated. A vector includes a nucleic acid (ordinarily RNA or DNA) to be expressed by the cell. This nucleic acid is optionally referred to as a "vector nucleic acid." A vector optionally includes materials to aid in achieving entry of the nucleic acid into the cell, such as a viral particle, liposome, protein coating or the like. A "cell transduction vector" is a vector which encodes a nucleic acid which is expressed in a cell once the nucleic acid is transduced into the cell.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

The term "subsequence" in the context of a particular nucleic acid sequence refers to a region of the nucleic acid equal to or smaller than the specified nucleic acid. A "recombinant nucleic acid" comprises or is encoded by one or more nucleic acids that are derived from a nucleic acid which was artificially constructed. For example, the nucleic acid can comprise or be encoded by a cloned nucleic acid formed by joining heterologous nucleic acids as taught, e.g., in Berger and Kimmel, *Guide to Molecular Cloning Techniques, Methods in Enzymology* volume 152 Academic Press, Inc., San Diego, Calif. (Berger) and in Sambrook et al. (1989) *Molecular Cloning—A Laboratory Manual* (2nd ed.) Vol. 1–3 (Sambrook). Alternatively, the nucleic acid can be synthesized chemically. The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell or a progenitor of the cell by artificial means.

The terms "isolated" or "biologically pure" refer to material which is substantially or essentially free from components which normally accompany it as found in its native state.

"Stringent hybridization" and "Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology— Hybridization with Nucleic Acid Probes* part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin per 50 mL at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4×SSC at 40° C. for 15 minutes. In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Myers and Miller, Computer Appl Biosci (now; Bioinformatics) 4:11–17 (1988); Smith and Waterman (1981) *Adv. Appl. Math.* 2: 482; Needleman and Wunsch (1970) *J. Mol. Biol.* 48: 443; Pearson and Lipman (1988) *Proc. Natl. Acad. Sci. USA* 85: 2444; Higgins and Sharp (1988) *Gene,* 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, for example, as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially an Fab with part of the hinge region (see, *Fundamental Immunology*, Third Edition, W. E. Paul, ed., Raven Press, NY (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies. Antibodies in the context of the present invention are optionally derived from libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314).

DETAILED DESCRIPTION OF THE INVENTION AND PREFERRED EMBODIMENTS

Proteins with a CAAX motif, such as Ras, a-factor and the γ-subunit of heterotrimeric G-protein, are post-translationally modified by prenylation of the cysteine, proteolytic removal of the terminal three residues and methylation-esterification of the newly-formed carboxyl group. A novel, farnesylation-dependent endoproteolytic activity named RACE (Ras and a-factor Converting Enzyme) was previously discovered. Numerous efforts to identify a CAAX protease gene responsible for the activity were unsuccessful. An autocrine arrest, sensitized selection for such mutants was developed. It involved ectopic expression of the a-factor receptor in a cells and utilized a CAAX sequence permutation defective for proteolysis. 127 mutants were isolated and characterized. 24 of these mutants had altered substrate specificity, of which 2 had novel alleles of RAM1. The remaining 22 had mutations in a single new gene, AFC1 (a-Factor Convertase).

Afc1p is the first identified farnesylation-dependent zinc metalloprotease. It is an integral membrane protein localized to internal membranes. Mutations in the HEXXH motif found in the protein, and characteristic of zinc metalloproteases, destroy Afc1p function. Null alleles of AFC1 are viable and produce lowered levels of mature a-factor. The residual pheromone produced by these cells implies the existence of multiple prenyl-dependent proteases. Ras2p with a proteolysis defective C-terminus has altered biological properties, suggesting that CAAX proteolysis is important for Ras function. Accordingly, AFC1 and the proteins encoded by the protein are attractive targets for therapeutics against Ras dependent cancers. Because of this, assays which can be used to detect the inhibition of AFC1 activity are of immediate commercial value to pharmaceutical companies.

RCE1 encodes a 315 amino acids long protein. Extensive searches against public molecular biology databases revealed no significant homologies to any known gene. Conceptual translation of the sequence obtained by mouse cDNA sequencing project (XREF Clone ID 331228, GenBank accession W14344, NCBI ID 521315) shows 46% identity on 49 aa stretch (63% positives) to Rce1p. The Rce1 protein sequence has limited similarity to sequence blocks characteristic of signal peptidases type II (SPase II), class A8 (lipoprotein signal peptidase, which recognize a conserved sequence and cuts in front of a cysteine to which a glyceride-fatty acid lipid is attached). Even though there is limited similarity, a consensus sequence for A8 SPase II is not present. Analysis of the Rce1 protein sequence predicts the presence of a number of transmembrane domains, suggesting that Rce1p is an integral membrane protein.

A deletion of RCE1 in haploid yeast cells of a-mating type has no effect on viability; however, it results in reduced a-factor halo size. Protease assays (see Ashby and Rine "Ras and a-Factor Converting Enzyme" (1995) *Methods in Enzymology* 230:235) detect reduced proteolytic activity in the membrane preparations from the RCE1 null strain. RCE1 deletion, combined with a deletion of AFC1, causes complete sterility of a cells due to a complete bloc in proteolytic processing of a-factor.

RCE1 seems to affect activity of yeast homologues of Ras oncoproteins. When deletion of RCE1 is combined with temperature-sensitive alleles of RAS2, it further decreases the viability of the yeast cells at elevated temperatures. The same deletion decreases the heat shock sensitivity of the yeast strains carrying an activated form of Ras protein RAS$^{val19}$. This allele is analogous to the mutation in the mammalian Ras–Ras$^{val12}$ found in a number of cancers. Yeast strains carrying the deletion also show increased intracellular localization of Ras2p (presumably to internal membranes) as measured by completely functional GFP-Ras2 fusions. All of this shows that RCE1 modulates activity of the yeast homologue of Ras oncoproteins, without completely inhibiting its activity. RCE1, therefore, is an attractive target for pharmaceutical treatments directed on reduction of elevated Ras activity, found in a many malignancies. Because of this, assays which can be used to detect the inhibition of RCE1, activity are of immediate commercial value to pharmaceutical companies for the identification of therapeutic compounds against Ras-mediated cancers.

Vectors, Cloning, Nucleic Acids and Proteins

The vectors of the invention include a vector nucleic acid, and optionally include components for packaging the vector nucleic acid to facilitate entry of the nucleic acid into a cell. The vector nucleic acid includes a nucleic acid subsequence which encodes a nucleic acid or protein of the invention. The subsequence is typically cloned into a cloning site in the vector nucleic acid which is designed to facilitate recombinant manipulation. A variety of commercially or commonly available vectors and vector nucleic acids can be converted into a vector of the invention by cloning a nucleic acid encoding a protein of the invention into the commercially or commonly available vector. A variety of common vectors suitable for this purpose are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids), Yeast Centromeric plasmids (the YCp series of plasmids) and pGPD-2. Expression in mammalian cells can be achieved using a variety of plasmids, including pSV2, pBC12BI, and p91023, as well as lytic virus vectors (e.g., vaccinia virus, adeno virus, and bacculovirus), episomal virus vectors (e.g., bovine papillomavirus), and retroviral vectors (e.g., murine retroviruses).

The nucleic acid sequence encoding a selected polypeptide is placed under the control of a promoter. A extremely wide variety of promoters are well known, and can be used in the vectors of the invention, depending on the particular application. Ordinarily, the promoter selected depends upon the cell in which the promoter is to be active. Other expression control sequences such as ribosome binding sites, transcription termination sites and the like are optionally included. For *E. coli*, example control sequences include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1,10 (Johnson and Davies (1984) *Mol. Cell. Biol.* 4:1440–1448) ADH2 (Russell et al. (1983) *J. Biol. Chem.* 258:2674–2682), PH05 (EMBO J. (1982) 6:675–680), and MFα1 (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). Multicopy plasmids with selective markers, such as LEU2, URA3, TRP1, and HIS3 is also commonly used. A number of yeast expression plasmids such as YEp6, YEp13, YEp4 can be used as expression vectors. A gene of interest can be fused, e.g., to any of the promoters in known yeast vectors. The above-mentioned plasmids have been fully described in the literature (Botstein et al. (1979) *Gene* 8:17–24; Broach, et al. (1979) *Gene,* 8:121–133). For a discussion of yeast expression plasmids, see, e.g., Parents, B., *YEAST* (1985), and Ausbel, Sambrook and Berger, all supra).

Given the strategy for making the vectors and nucleic acids of the present invention, one of skill can construct a variety of vectors and nucleic acid clones containing functionally equivalent nucleic acids. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology,* F.M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acids provided by this invention, whether RNA, cDNA, genomic DNA, or a hybrid of the various combinations, are isolated from biological sources or synthesized in vitro. The nucleic acids and vectors of the invention are present in transformed or transfected whole cells, in transformed or transfected cell lysates, or in a partially purified or substantially pure form.

In vitro amplification techniques suitable for amplifying sequences to provide a nucleic acid, or for subsequent analysis, sequencing or subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids are summarized in Cheng et al. (1994) *Nature* 369: 684–685 and the references therein. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

Oligonucleotides for in vitro amplification methods or for use as gene probes, for example, are typically chemically synthesized according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

The polypeptides of the invention can be synthetically prepared in a wide variety of well-know ways. For instance, polypeptides of relatively short length can be synthesized in solution or on a solid support in accordance with conventional techniques. See, e.g., Merrifield (1963) *J. Am. Chem. Soc.* 85:2149–2154. Various automatic synthesizers are commercially available and can be used in accordance with known protocols. See, e.g., Stewart and Young (1984) *Solid Phase Peptide Synthesis*, 2d. ed., Pierce Chemical Co. As described in more detail herein, the polypeptide of the invention are most preferably made using recombinant techniques, by expressing the polypeptides in host cells and purifying the expressed proteins.

In a preferred embodiment, the polypeptides, or subsequences thereof, are synthesized using recombinant DNA methodology. Generally this involves creating a DNA sequence that encodes the protein, through recombinant, synthetic, or in vitro amplification techniques, placing the DNA in an expression cassette under the control of a particular promoter, expressing the protein in a host cell, isolating the expressed protein and, if required, renaturing the protein.

Once a nucleic acid encoding a polypeptide of the invention is isolated and cloned, the nucleic acid is optionally expressed in recombinantly engineered cells known to those of skill in the art. Examples of such cells include bacteria, yeast, plant, filamentous fungi, insect (especially employing baculoviral vectors), and mammalian cells. The recombinant nucleic acids are operably linked to appropriate control sequences for expression in the selected host. For *E. coli*, example control sequences include the T7, trp, or lambda promoters, a ribosome binding site and preferably a transcription termination signal. For eukaryotic cells, the control sequences typically include a promoter and preferably an enhancer derived from immunoglobulin genes, SV40, cytomegalovirus, etc., and a polyadenylation sequence, and optionally include splice donor and acceptor sequences.

Plasmids of the invention can be transferred into the chosen host cell by well-known methods such as calcium chloride transformation for *E. coli* and calcium phosphate treatment or electroporation for mammalian cells. Yeast transformation is conveniently performed by one of two common procedures. In one procedure, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in Beggs (1978) *Nature* (London) 275:104–109, and Hinnen, et al. (1978) *Proc. Nati. Acad. Sci. USA* 75:1929–1933. The second procedure does not involve removal of the cell wall. Instead, the cells are treated, e.g., with lithium chloride or acetate and PEG and put on selective plates (Ito, et al. (1983) *J. Bact.* 153:163–168).

Cells transformed by plasmids can be selected by resistance to antibiotics conferred by genes contained on the plasmids, such as the amp, gpt, neo and hyg genes. Viral vectors of the invention transduce nucleic acids into cells within the host range of the viral vector.

Once expressed, the recombinant polypeptides can be purified according to standard procedures of the art, including ammonium sulfate precipitation, affinity columns, column chromatography, gel electrophoresis and the like (see, generally, R. Scopes, *Polypeptide Purification*, Springer-Verlag, N.Y. (1982), Deutscher, *Methods in Enzymology* Vol. 182: *Guide to Polypeptide Purification.*, Academic Press, Inc. NY (1990)). Once purified, partially or to homogeneity as desired, the polypeptides may then be used (e.g., as immunogens for antibody production).

After chemical synthesis, biological expression or purification, the polypeptide(s) may possess a conformation substantially different than the native conformations of the constituent polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (See, Debinski et al. (1993) *J. Biol. Chem.*, 268: 14065–14070; Kreitman and Pastan (1993) *Bioconjug. Chem.*, 4: 581–585; and Buchner, et al., (1992) *Anal. Biochem.*, 205: 263–270). Debinski et al., for example, describe the denaturation and reduction of inclusion body polypeptides in guanidine-DTE. The polypeptide is then refolded in a redox buffer containing oxidized glutathione and L-arginine.

One of skill will recognize that modifications can be made to the polypeptides without diminishing their biological activity. Some modifications may be made to facilitate the cloning, expression, or incorporation of the targeting molecule into a fusion polypeptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Making Conservative Modifications of the Nucleic Acids and Polypeptides of the Invention One of skill will appreciate that many conservative variations of the polypeptides and vectors disclosed yield essentially identical polypeptides and vectors. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively substituted variations of each disclosed sequence are a feature of the present invention.

One of skill will recognize many ways of generating alterations (introducing mutations) in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook, Innis, Ausbel, Berger, Needham VanDevanter and Mullis (all supra).

Most commonly, amino acid sequences are altered by altering the corresponding nucleic acid sequence and expressing the polypeptide. However, polypeptide sequences are also optionally generated synthetically on commercially available peptide synthesizers to produce any desired polypeptide (see, Merrifield, and Stewart and Young, supra). General knowledge regarding the nature of proteins and nucleic acids allows one of skill to select appropriate sequences with activity similar or equivalent to the nucleic acids, vectors and polypeptides disclosed herein. The definitions section herein describes exemplar conservative amino acid substitutions.

Most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Human Homologues of AFC1 and RCE1

The present invention provides for mammalian homologues to the yeast AFC1 and RCE1 genes. A Genbank search for nucleic acids encoding sequences similar to the proteins encoded by the respective genes revealed expression sequence tags (ESTs) with homology to the yeast genes. The entries are found at accession number z43273 (a partial cDNA encoding a human protein with similarity to AFC1) and w14344 (a partial cDNA encoding a mouse protein with similarity to RCE1).

Complete mammalian homologues to AFC1 and RCE1 are isolated in a variety of ways. In one embodiment, the Afc1p or Rce1p polypeptides, or polypeptides encoded by the identified mammalian sequences, are used to raise antibodies as described herein. The antibodies are used to screen expression libraries for polypeptides with homology to the immunogen used to raise the antibody. Thus, the invention provides an isolated clone encoding a polypeptide which binds to an antibody encoded by a mammalian AFC1 or RCE1 homologue.

In another embodiment, the nucleic acids encoded by the yeast AFC1 or RCE1 genes, or mammalian nucleic acids encoded by the GenBank nos z43273 or w14344 are labeled and hybridized to a mammalian cDNA or genomic DNA library under increasingly stringent conditions. Clones which hybridize under moderate to stringent conditions are homologous to the probe sequences. Preferred clones hybridize to the selected labeled nucleic acid under stringent conditions. Mammalian cDNA and genomic libraries are widely available, and methods of hybridizing nucleic acids to the libraries are well known.

In yet another embodiment, the invention provides PCR probes which are used to amplify a mammalian AFC1 or RCE1 homologue from a library or tissue sample. Most typically, amplification primers are between 8 and 100 nucleotides in length, and preferably between about 10 and 30 nucleotides in length. More typically, the primers are between about 15 and 25 nucleic acids in length. One of skill will recognize that the 3' end of an amplification primer is more important for PCR than the 5' end. Investigators have reported PCR products where only a few nucleotides at the 3' end of an amplification primer were complementary to a DNA to be amplified. In this regard, nucleotides at the 5' end of a primer can incorporate structural features unrelated to the target nucleic acid; for instance, in one embodiment, a sequencing primer hybridization site (or a complement to such as primer, depending on the application) is incorporated into the amplification primer, where the sequencing primer is derived from a primer used in a standard sequencing kit, such as one using a biotinylated or dye-labeled universal M13 or SP6 primer. Alternatively, the primers optionally incorporate restriction endonuclease sites. The primers are selected so that there is no complementarity between any known sequence which is likely to occur in the sample to be amplified and any constant primer region. One of skill will appreciate that constant regions in primer sequences are optional.

Typically, all primer sequences are selected to hybridize only to a perfectly complementary DNA, with the nearest mismatch hybridization possibility from known DNA sequences which are likely to occur in the sample to be amplified having at least about 50 to 70% hybridization mismatches to sequences which are known to be in the sample and which do not encode a nucleic acid of the invention, and preferably 100% mismatches for the terminal 5 nucleotides at the 3' end of the primer. Alternatively, a series of degenerate primers with universal base acceptors at ambiguous codon positions are used in parallel reactions to amplify a nucleic acid.

The primers are selected so that no secondary structure forms within the primer. Self-complementary primers have poor hybridization properties, because the complementary portions of the primers self hybridize (i.e., form hairpin structures). The primers are also selected so that the primers do not hybridize to each other, thereby preventing duplex formation of the primers in solution, and possible concatenation of the primers during PCR. If there is more than one constant region in the primer, the constant regions of the primer are selected so that they do not self-hybridize or form hairpin structures.

Where sets of amplification primers (i.e., the 5' and 3' primers used for exponential amplification) are of a single length, the primers are selected so that they have roughly the same, and preferably exactly the same overall base composition (i.e., the same A+T to G+C ratio of nucleic acids). Where the primers are of differing lengths, the A+T to G+C ratio is determined by selecting a thermal melting temperature for the primer-DNA hybridization, and selecting an A+T to G+C ratio and probe length for each primer which has approximately the selected thermal melting temperature.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector program from Kodak. In addition to commercially available programs for primer selection, one of skill can easily design simple programs for any of the preferred selection steps. Amplification primers can be selected to provide amplification products that span specific deletions, truncations, and insertions in an amplification target, thereby facilitating the detection of specific abnormalities such as a transposon insertion as described herein.

Antibodies to Afc1p and to Rce1p

Antibodies are raised to Afc1p and Rce1p polypeptides of the present invention, including individual, allelic, strain, or species variants, and fragments thereof, both in their naturally occurring (full-length) forms and in recombinant forms. Additionally, antibodies are raised to these polypeptides in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A number of immunogens are optionally used to produce antibodies specifically reactive with Afc1p and Rce1p polypeptides. Recombinant or synthetic polypeptides of 10 amino acids in length, or greater, typically 20 amino acids in length, or greater, more typically 30 amino acids in length, or greater, selected from amino acid sub-sequences of Afc1p and Rce1p are the preferred polypeptide immunogen for the production of monoclonal or polyclonal antibodies. In one class of preferred embodiments, an immunogenic peptide conjugate is also included as an immunogen. Naturally occurring polypeptides are also used either in pure or partially pure form.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen (antigen), preferably a purified polypeptide, a polypeptide coupled to an appropriate carrier (e.g., GST, keyhole limpet hemanocyanin, etc.), or a polypeptide incorporated into an immunization vector, such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired (see, e.g., Coligan (1991) *Current Protocols in Immunology* Wiley/Greene, NY; and Harlow and Lane (1989) *Antibodies: A Laboratory Manual* Cold Spring Harbor Press, NY).

Antibodies, including binding fragments and single chain recombinant versions thereof, against whole or predetermined fragments of Afc1p or Rce1p are raised by immunizing animals, e.g., with conjugates of the fragments with carrier proteins as described above. Typically, the immunogen of interest is a peptide of at least about 10 amino acids, more typically the peptide is 20 amino acids in length, generally the fragment is 25 amino acids in length and often the fragment is 30 amino acids in length or greater. The peptides are optionally coupled to a carrier protein (e.g., as a fusion protein), or are recombinantly expressed in an immunization vector. Antigenic determinants on selected peptides to which antibodies bind are typically 3 to 10 amino acids in length.

Monoclonal antibodies are prepared from cells secreting the desired antibody. These antibodies are screened for binding to normal or modified polypeptides, or screened for agonistic or antagonistic activity, e.g., activity mediated through a selected polypeptide. Specific monoclonal and polyclonal antibodies will usually bind with a $K_D$ of at least about 0.1 mM, more usually at least about 50 $\mu$M, and preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314).

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention are also used for affinity chromatography in isolating natural or recombinant Afc1p or Rce1p polypeptides. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified polypeptides are released.

In one highly preferred embodiment, the antibodies are used to screen expression libraries for particular expression products such as homologous proteins to the yeast Afc1p or Rce1p proteins, e.g., in an expression library from human or other mammalian tissue. Optionally, the antibodies in such a procedure are labeled with a moiety allowing easy detection of presence of antigen by antibody binding.

Antibodies raised against polypeptides can also be used to raise anti-idiotypic antibodies. These are useful for detecting abnormal growth related to the presence of the respective polypeptides.

Antibodies are optionally humanized. Humanized (chimeric) antibodies are immunoglobulin molecules comprising a human and non-human portion. The antigen combining region (or variable region) of a humanized chimeric antibody is derived from a non-human source (e.g., murine) and the constant region of the chimeric antibody (which confers biological effector function, such as cytotoxicity, to the immunoglobulin) is derived from a human source. The humanized chimeric antibody has the antigen binding specificity of the non-human antibody molecule and the effector function conferred by the human antibody molecule. A large number of methods of generating chimeric antibodies are well known to those of skill in the art (see, e.g., U.S. Pat. Nos: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

In another embodiment, this invention provides for fully human antibodies against Afc1p or Rce1p polypeptides. Human antibodies consist entirely of characteristically human immunoglobulin sequences. The human antibodies of this invention can be produced in using a wide variety of methods (see, e.g., Larrick et al., U.S. Pat. No. 5,001,065, for a review). A general approach for producing human antibodies by trioma technology is described by Ostberg et al. (1983), *Hybridoma* 2: 361–367, Ostberg, U.S. Pat. No. 4,634,664, and Engelman et al., U.S. Pat. No. 4,634,666. Other approaches include immunization of mice transformed to express human immunoglobulin genes, and phage display screening (Vaughan et al. supra.).

Afc1p and Rce1p Polypeptide Assays

The expression of selected polypeptides (e.g., Afc1p, Rce1p and conservative modifications thereof) can also be detected and/or quantified by detecting or quantifying the expressed polypeptide. As described herein, detection of the various polypeptides of the invention is a feature of certain assays of the invention.

The polypeptides can be detected and quantified by any of a number of means well known to those of skill in the art. These include analytic biochemical methods, such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay(RIA), enzyme-linked immunosorbent assays (ELISAs), immunofluorescent assays, western blotting, and the like.

In a particularly preferred embodiment, the polypeptides are detected in an electrophoretic protein separation, more preferably in a two-dimensional electrophoresis, while in a most preferred embodiment, the polypeptides are detected using an immunoassay.

As used herein, an immunoassay is an assay that utilizes an antibody to specifically bind to the analyte (e.g., selected polypeptide, such as Afc1p or Rce1p). The immunoassay is thus characterized by detection of specific binding of a polypeptide to an anti-polypeptide antibody, as opposed to the use of other physical or chemical properties to isolate, target, and quantify the analyte.

As indicated above, the presence or absence of polypeptides in a biological sample can be determined using electrophoretic methods. Means of detecting proteins using electrophoretic techniques are well known to those of skill in the art (see generally, R. Scopes (1982) *Protein Purification,* Springer-Verlag, NY; Deutscher, (1990) *Methods in Enzymology* Vol. 182: *Guide to Protein Purification.,* Academic Press, Inc., NY).

In a preferred embodiment, the polypeptides are detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume* 37: *Antibodies in Cell Biology,* Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte. The capture agent is a moiety that specifically binds to the analyte. In a preferred embodiment, the capture agent is an antibody that specifically binds polypeptide(s) or polypeptide subsequences (e.g., antigenic domains which specifically bind to the antibody). In a second preferred embodiment, the capture agent is the polypeptide and the analyte is antisera comprising an antibody which specifically binds to the polypeptide.

Immunoassays often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled anti-polypeptide antibody. Alternatively, the labeling agent may be a third moiety, such as another antibody, that specifically binds to the antibody/polypeptide complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as streptococcal protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401–1406, and Akerstrom, et al. (1985) *J. Immunol.,* 135: 2589–2542).

Throughout the assays, incubation and/or washing steps are optionally performed after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Immunoassays for detecting polypeptides may be either competitive or noncompetitive. Noncompetitive immunoassays are assays in which the amount of captured analyte is directly measured. In one preferred "sandwich" assay, for example, the capture agent can be bound directly to a solid substrate where they are immobilized. The immobilized capture agent then captures analyte present in the test sample. The analyte thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

In competitive assays, the initial amount of analyte present in the sample is measured indirectly by measuring the amount of an added (exogenous) analyte displaced (or competed away) from a capture agent by the analyte present in the sample. In one competitive assay, a known amount of, in this case, analyte is added to the sample and the sample is then contacted with a capture agent. The amount of exogenous analyte bound to the capture agent is inversely proportional to the initial analyte present in the sample.

In a preferred embodiment, western blot (immunoblot) analysis is used to detect and quantify the presence of selected polypeptides in the sample. The technique generally comprises separating sample proteins by gel electrophoresis on the basis of molecular weight, transferring the separated proteins to a suitable solid support (such as a nitrocellulose filter, a nylon filter, or derivatized nylon filter) and incubating the sample with the antibodies that specifically bind the selected polypeptide. The antibodies specifically bind to polypeptide on the solid support. These antibodies are optionally directly labeled or alternatively are optionally subsequently detected using labeled antibodies (e.g., labeled sheep anti-mouse antibodies) that specifically bind to the selected polypeptide.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41). Enzyme linked assays (e.g., ELISA assays) are also preferred.

The assays of this invention as scored (as positive or negative for a selected polypeptide) according to standard methods well known to those of skill in the art. The particular method of scoring will depend on the assay format and choice of label. For example, a western blot assay can be scored by visualizing the colored product produced by the enzymatic label. A clearly visible colored band or spot at the correct molecular weight is scored as a positive result, while the absence of a clearly visible spot or band is scored as a negative. In a preferred embodiment, a positive test will show a signal intensity (e.g., polypeptide quantity) at least twice that of the background and/or control and more preferably at least 3 times or even at least 5 times greater than the background and/or negative control.

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin.

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

As mentioned above, depending upon the assay, various components, including the antigen, target antibody, or anti-antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas (1970) *J. Biol. Chem.* 245 3059).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

Screening for Nucleic Acids and the Use of Nucleic Acids as Molecular Probes

The nucleic acids of the invention (e.g., AFC1, RCE1, homologoues thereof, and conservative modifications thereof) are useful as molecular probes, in addition to their utility in encoding the polypeptides described herein. As set forth supra, certain assays of the invention include the detection of AFC1 or RCE1 expression.

Typically, probes derived from the exemplar nucleic acids are used to detect and/or quantitate the presence of complementary nucleic acid in a selected biological sample. A wide variety of formats and labels are available and appropriate for nucleic acid hybridization, including those reviewed in Tijssen (1993) *Laboratory Techniques in biochemistry and molecular biology—hybridization with nucleic acid probes* parts I and II, Elsevier, N.Y. and Choo (ed) (1994) *Methods In Molecular Biology Volume 33—In Situ Hybridization Protocols* Humana Press Inc., New Jersey (see also, other books in the Methods in Molecular Biology series); see especially, Chapter 21 of Choo (id) "Detection of Virus Nucleic Acids by Radioactive and Nonisotopic in Situ Hybridization".

For instance, PCR is routinely used to detect nucleic acids in biological samples (see, Innis, supra, for a general description of PCR techniques). Accordingly, in one class of embodiments, the nucleic acids of the invention are used as PCR primers or templates, or as positive controls in PCR reactions for the detection of in a biological sample. Briefly, nucleic acids with sequence identity or complement arity to an exemplar sequence is used as templates to synthetically produce oligonucleotides of about 15–25 nucleotides with sequences similar or identical to the complement of a the selected nucleic acid subsequence. The oligonucleotides are then used as primers in PCR reactions to detect selected nucleic acids in biological samples. A nucleic acid of the invention (i.e., a cloned nucleic acid corresponding to the region to be amplified) is also optionally used as an amplification template in a separate reactions as a positive control to determine that the PCR reagents and hybridization conditions are appropriate.

Other methods for the detection of nucleic acids in biological samples using nucleic acids of the invention include Southern blots, northern blots, in situ hybridization (including Fluorescent in situ hybridization (FISH), and a variety of other techniques overviewed in Choo (supra)). A variety of automated solid-phase detection techniques are also appropriate. For instance, very large scale immobilized polymer arrays (VLSIPS™) are used for the detection of nucleic acids. See, Tijssen (supra), Fodor et al. (1991) *Science*, 251: 767–777; Sheldon et al. (1993) *Clinical Chemistry* 39(4): 718–719 and Kozal et al. (1996) *Nature Medicine* 2(7): 753–759.

Therapeutic Uses for Afc1p and Rce1p Inhibitors

In one aspect, the present invention provides therapeutics for treating cancers such as tumors which are correlated to Ras activation. In the therapeutic methods of the invention, a small molecule inhibitor of a mammalian Afc1p or Rce1p protein, such as NMe181, is administered to a patient suffering from cancer and, in particular, cancer associated with an activated Ras oncogene.

Administration is by any of the routes normally used for introducing a molecule into ultimate contact with blood or tissue cells. Administration is made in any suitable manner, preferably with pharmaceutically acceptable excipients. Suitable methods of administering inhibitors in the context of the present invention to a patient are available. Intramuscular, subcutaneous and parenteral administration such as intravenous administration are suitable methods of administration. Where the inhibitor is administered to inhibit growth of a tumor, the inhibitor is often administered to the site of the tumor, rather than by systemic introduction. However, systemic introduction is optionally used. Formulations of compositions to be administered can be presented in unit-dose or multi-dose sealed containers, such as ampules and vials.

Pharmaceutically acceptable excipients are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The dose administered to a patient, in the context of the present invention should be sufficient to effect a beneficial therapeutic response in the patient over time, such as a reduction in the rate of tumor growth, or more preferably, a reduction in tumor size. The dose will be determined by the efficacy of the particular inhibitor employed and the condition of the patient, as well as the body weight or surface area of the patient to be treated. The size of the dose also will be determined by the existence, nature, and extent of any adverse side-effects that accompany the administration of a particular inhibitor.

In determining the effective amount of the inhibitor, the physician evaluates circulating plasma levels of the inhibitor, toxicities, progression of the disease, and the production of antibodies to the particular inhibitor.

For administration, inhibitors can be administered at a rate determined by the LD-50 of the inhibitor and the side-effects of the inhibitor at various concentrations, as applied to the mass and overall health of the patient. Administration can be accomplished via single or divided doses.

If a patient undergoing infusion of an inhibitor develops fevers, chills, or muscle aches, he/she typically receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Infusion is slowed or discontinued depending upon the severity of the reaction.

The effect of the therapeutic inhibitors are measured by monitoring the size of a tumor or the extent of metastasis before treatment, and comparing the size of the tumor or extent of metastasis in a patient over time. Typically, measurements are taken before, during and after the therapeutic regimen.

Kits

The present invention provides a variety of kits for the detection of AFC1 or RCE1 nucleic acids or proteins, and for the testing compounds for their ability to inhibit AFC1 or RCE1 expression, or Afc1p or Rce1p protein activity.

Detection kits preferably include one or more reagents for determining the presence or absence of a selected nucleic acid or protein, i.e., any of the nucleic acids or proteins described herein. Preferred reagents include nucleic acid probes that specifically hybridize to the exemplar sequences, or subsequence thereof; probes that specifically bind to an abnormal genes (e.g., one containing premature truncations, insertions, or deletions), and antibodies that specifically bind to polypeptides or subsequences thereof. The antibody or hybridization probe may be free or immobilized on a solid support such as a test tube, a microtiter plate, a dipstick and the like. The kit optionally include instructional materials teaching the use of the antibody or hybridization probe in an assay for the detection of the relevant nucleic acid or protein, a container or other packaging material or the like.

The kits optionally include alternatively, or in combination with any of the other components described herein, an antibody which specifically binds a polypeptide of the invention. The antibody can be monoclonal or polyclonal. The antibody can be conjugated to another moiety such as a label and/or it can be immobilized on a solid support (substrate).

The kits can also optionally include a second antibody for detection of polypeptide/antibody complexes or for detection of hybridized nucleic acid probes. The kits optionally include appropriate reagents for detection of labels, positive and negative controls, washing solutions, dilution buffers and the like.

Kits testing for inhibition of RCE1, or AFC1 expression optionally include any of the components described above for detecting nucleic acids or proteins. Kits testing for Afc1p or Rce1p activity can monitor the proteolytic cleavage of the terminal AAX peptide from a relevant CAAX protein such as Ras. This can be accomplished by monitoring the change in electrophoretic mobility, e.g., in a western blot or ELISA assay. These kits optionally include any of the following: reagents for detecting a CAAX protein (e.g., anti-Ras antibodies), electrophoretic equipment, instructions in the detection of AAX cleavage or the like. Other assays for monitoring protease activity are described in Ashby and Rine "Ras and a-Factor Converting Enzyme" (1995) *Methods in Enqmology* 230:235.

In addition to monitoring AAX cleavage directly, the present invention provides for the detection of AAX cleavage using a functional assay. For example, as described herein, a heat-shock assay can be used to monitor prenylation-dependent Ras activity. Kits optionally include any of the components used in such an assay, including yeast strains such as ΔAFC1 or ΔRCE1, instructions, containers, growth media, control yeast strains, thermocycling equipment, water baths for administering the heat shock, and the like.

Discussion of the Accompanying Sequence Listing

SEQ ID NO:1 provides the sequence of the AFC1 gene from yeast. SEQ ID NO:3 provides the sequence of the RCE1 gene from yeast. In each case, the information is presented as a DNA sequence. One of skill will readily understand that the sequence also describes the corresponding RNA (i.e., by substitution of the T residues with U residues) and a variety of conservatively modified variations thereof. In addition, the nucleic acid sequence provides the corresponding amino acid sequence by translating the given DNA sluence using the genetic code.

SEQ ID NO:2 provides the protein sequence of the Afc1p protein from yeast. SEQ ID NO:4 provides the sequence of the Rce1p protein from yeast. In each case, the information is presented as a polypeptide sequence. One of skill will readily understand that the sequences also describe all of the corresponding RNA and DNA sequences which encode the protein, by conversion of the amino acid sequence into the corresponding nucleotide sequence using the genetic code, by alternately assigning each possible codon in each possible codon position. The sequences also provides a variety of conservatively modified variations by substituting appropriate residues with the exemplar conservative amino acid substitutions provided, e.g., in the Definitions section above.

EXAMPLES

The following examples are provided by way of illustration only and not by way of limitation. Those of skill will readily recognize a variety of noncritical parameters which can be changed or modified to yield essentially similar results.

To evaluate the functional role of Ras CAAX proteolysis, naturally occurring CAAX sequences from rabbit skeletal muscle phosphorylase kinase were utilized. The α and β subunits of this holoenzyme contain CAAX sequences that in vivo are prenylated, yet do not undergo further processing (Heilmeyer, et al., *Proc. Natl. Acad. Sci. USA*, 89(20) :9554–9558 (1992)). It has now been demonstrated that peptides containing these sequences are not proteolytically cleaved in vitro by the membrane-bound CAAX protease. These same peptides do, however, bind to the protease as defined by their ability to compete for proteolysis of peptides with normally processed CAAX sequences.

The issue regarding whether CAAX proteolysis and methylation are required for yeast Ras2p function has been addressed. To do so, a highly sensitive and reproducible assay of Ras2p function has been developed. One of the hallmark phenotypes of activating mutations in yeast Ras2p is the inability of the cells to properly enter stationary phase resulting in poor viability and heat shock sensitivity. Current heat shock assays to assess Ras activation utilize plate assays where a large number of cells being tested are transferred to plates that have been prewarmed to 55° C. The plates are then incubated at 55° C. for various times up to one hour. After a subsequent incubation at 30° C. for about 18 hours, the strains are scored for yeast death or growth and, thus, heat shock sensitivity or resistance, respectively. This assay is adequate for crude measurements of heat shock sensitivity, but, unfortunately, it is clearly inadequate for quantitating intermediate degrees of heat shock sensitivity.

As such, an improved assay of Ras2p function has been developed. This assay utilizes liquid-based heat shock of the yeast strains in, for example, a programmable thermocycle (PCR) machine or other water-bath. Generally, cells are grown in a liquid medium into a stationary phase. The liquid medium can be water or some other growth medium, such as the commercially available Yeast Minimal Medium (See, e.g., Atlas, et al., *HANDBOOK OF MICROBIOLOGICAL MEDIA* (CRC Press, Ann Arbor, Mich. (1993); see also, Sambrook, Ausbel and Berger, all supra). Equal amounts of cells are added to tubes containing the liquid medium, preferably water. At the same time, portions of these suspensions are plated on the growth media to score the viability before the heat shock, i.e., to serve as controls. The tubes are then placed in a PCR machine or a water-bath at a temperature ranging between about 40° C. and about 60° C., more preferably at a temperature between 50° C. and 55° C., and heat shocked for a time period ranging from about 0.5 minute to about 20 minutes, more preferably for a time period from about 3 minutes to about 12 minutes. It will be readily apparent to those of skill in the art that the specific reaction conditions employed will depend upon the amount of cells in the suspension and upon how deep into the stationary phase the tested cells are.

The heat-treated cells are then cooled down to a temperature ranging from 0° C. to about 30° C., more preferably to about room temperature (20° C.), and plated on the growth media to score viability after the heat shock. The ratio of the number of survivors in the tested strain (e.g., a strain carrying deletions in AFC1 or RCE1 or alterations in the RAS2 C-terminus CAMQ sequence) to the number of survivors in the control strain (i.e., the strain which has no deletions or alterations) defines the level of suppression of heat shock sensitivity. At the same time, the strains with plasmids carrying the wild type RAS2 gene are also tested for heat shock sensitivity to determine if the introduced changes by themselves have any effect on the rate of survival.

To determine the functional impact of blocking Ras2p CAAX proteolysis, the normal Ras2p CAAX sequence CIIS with replaced with CAMQ or CLVS using site-directed mutagenesis. These non-proteolyzable sequences reduced the activated phenotype of cells approximately 100-fold. In contrast, the presence of these non-proteolyzable CAAX sequences did not have any detectable phenotype in non-activated forms of Ras2p. These results are the first demonstration of a functional requirement of Ras-CAAX proteolysis and indicate that this aspect of Ras processing represents a pharmacological target in tumors containing activating mutations in Ras.

In addition to testing the effects of the non-proteolyzable rabbit phosphorylase kinase CAAX sequences CAMQ and CLVS on Ras2p function, the importance of Ras2p C-terminal methylation was also tested. The STE14 gene product has been shown to encode the prenylated protein C-terminal methyltransferase that processes both the Ras2p protein and the pheromone a-factor (Hrycyna, et al., *EMBO J.*, 10:1699–1709 (1991)). Deletion of the STE14 structural gene results in an absence of detectable Ras2p methylation, but does not effect activated Ras2p heat shock sensitivity when evaluated with the standard plate heat shock assay (Id.).

The importance of C-terminal methylation of activated Ras2$^{val19}$ was assessed in a strain in which the STE14 gene was replaced with the LEU2 gene (ste14Δ::LEU2) in the liquid-based heat shock assay described above. As was the case with blocking CAAX proteolysis with the CAMQ or CLVS substitution, preventing C-terminal methylation reduced heat shock sensitivity greater than 50-fold. This result indicated that blocking activated Ras2p methylation significantly reduced Ras2p function and, thus, attenuated the activated phenotype. This result is the first demonstration of the functional relevance of Ras2p farnesylated cysteine methylation.

In addition to the foregoing, the issue of whether the effects of blocking Ras2p proteolysis and blocking Ras2p methylation would be additive when combined was tested. For this experiment, heat shock sensitivities in strains with wild-type or activated forms of Ras2p with various CAAX sequences in the presence or absence of the STE14 gene were compared. The results indicate that the heat shock resistance conferred by the non-proteolyzable CAAX sequence together with the absence of the STE14 gene (ste14Δ::LEU2) does not result in an increased heat shock resistance beyond that of each component alone. These data therefore support the notion that CAMQ and CLVS represent non-proteolyzable sequences and that the two phenotypes, namely heat shock resistance in Ras2$^{val19}$ CAMQ or CLVS and heat shock resistance in the Ras2$^{val19}$ (ste14Δ::LEU2) strains, are epistatic.

As a means to isolate mutants in CAAX processing, a powerful genetic selection for mutants defectivein a-factor processing was performed. The a-factor pheromone is another CAAX containing peptide that is processed by the same protein:farnesyltransferase and methyltransferase enzymes as Ras2p. The genetic selection produced a novel mutant that displayed a differential phenotype depending upon the particular AAX extension of the CAAX sequence. This mutant possessed a single mutation that was responsible for the phenotype and the corresponding gene was cloned by complementation. The gene, named AFC1 for a-Factor Convertase, contains an amino acid sequence motif identified as the active site in several characterized zinc metalloproteases. This property is consistent with both the in vitro proteolysis defect of the corresponding mutant and the o-phenanthroline sensitivity of this activity in wild-type extracts. Furthermore, this a-factor CAAX protease was dependent upon a farnesylated substrate as expected of a protease that processes a-factor in vivo. The isolation of AFC1 represents the first CAAX protease to be identified. A genetic knockout of AFC1 resulted in a significant, but not complete, reduction of a-factor production, thereby exposing the presence of a second CAAX protease. Using a similar approach, a second CAAX protease was identified. This gene for the second protease has been named RCE1 (Ras and a-Factor Converting Enzyme).

Example 1

Autocnine Arrest Selection

Autocrine arrest selection was designed to simplify the task of identifying mutants that are defective in the production of yeast mating pheromone-a-factor. This assay relies on the fact that haploid yeast cells of both a and a mating types share the same mating signal transduction pathway. The mating specificity is defined only by the type of mating pheromone receptor that is expressed on the surface of the cell. Expression of the a-factor receptor in a cell producing biologically active a-factor will lead to autocrine arrest. Mutants having mutations in the genes responsible for either a-factor production or for transduction of the mating signal will be able to escape the arrest, grow and form colonies.

A. Strain Design

The SST2 gene (mutations in this gene confer supersensitivity to the mating pheromone, thereby allowing tighter arrest) was deleted using a two-step gene replacement in the JRY3658 strain (W303 HMLΔp, HMRΔp, MATΔp). A plasmid carrying the MATα locus was introduced in the JRY3658 Δsst2 strain allowing it to mate as an α strain. JRY3658 Δsst2 pMATα was crossed to JRY527 Δmfa1::hisG, mfa2Δ::hisG. The diploid was sporulated and the segregant of the following genotype was identified: HMLaΔp, HMRaΔp, MATaΔp, Δmfa1::hisG, mfa2Δ::hisG, Δsst2, his3, lys2, leu2–3,112, ura3.

The gene encoding the a-factor receptor (i.e., STE3) was placed under the control of the inducible GAL promoter, thereby allowing the expression of the gene to be controlled by the type of carbon source in the growth medium. This construct was integrated in the STE3 locus of the strain described above. A plasmid carrying MFA1 gene with the altered C-terminal CAAX sequence, i.e., CAMQ, was used as a source of the mating pheromone. This sequence was introduced by site directed mutagenesis.

B. Selection

In each round of selection, 20 independent colonies were picked and grown at 30° C. in the supplemented minimal media. Equal numbers of cells from each culture were mutagenized by UV light in liquid. The mutagenized cells were transferred back into the growth media and grown overnight at room temperature to overcome the phenotypic lag. Cells were plated on plates containing galactose to induce expression of the a-factor receptor construct, and incubated at room temperature.

C. Identification of the Mutants

All colonies formed on galactose-containing media were scored for a-factor production in halo assays. Mutant strains which produced no or very little of the a-factor were used in a secondary screen. In the secondary screen, patches of cells were treated with synthetic alpha factor to eliminate all the mutants in the mating signal transduction pathway. Strains which were able to arrest (indicating that they were able to grow on galactose not because they couldn't respond to the pheromone) were used in complementation tests. The mutants were crossed to the strains with defects in the genes known to be involved in production of a-factor (i.e., ram1—a subunit of the farnesyltransferase, ste14—methyltransferase and ste6—a-factor transporter). The strains which were complemented by all the mutant strains were used in another complementation test, using plasmids carrying the a-factor processing genes (i.e., RAM1, RAM2, STE14 and STE6).

The mutant strains which passed both complementation tests were analyzed for substrate specific processing defects. The plasmid with the MFA1(CAMQ) variant, used in the selection, was cured from the strains and a wild type MFA1(CVIA) gene carrying plasmid was introduced. The mutant strains which produced no a-factor with MFA1 (CAMQ) plasmid and which were able to produce detectable amounts of biologically active a-factor with MFA1 (CVIA) formed a large complementation group termed AFC1 (a-Factor Convertase). The gene defined by this complementation group was cloned using a multicopy genomic library by complementation of the mutant phenotype (a-factor production). The RCE1 (Ras and a-Factor Converting Enzyme) was identified as a partial multicopy suppressor of the afc1 MFA1 (CAMQ) dependent mutant phenotype.

Example 2

Heat Shock Sensitiviy Assay

The heat shock sensitivity assay is used to determine if changes introduced in the yeast strain have any effects on Ras signaling. This assay utilizes a dominant, hyperactivated allele of RAS2, i.e., RAS2$^{val19}$. Cells carrying the RAS2$^{val19}$ allele on a CEN plasmid are significantly more sensitive to the short term heat treatment then wild type strains. The assay can be performed in many different ways. The goal of the assay is to evaluate the number of cells able to survive the heat shock.

The original assay involves streaaing similar numbers of cells on a plate which is then placed in a water-bath at a temperature of about 50° to 55° C. for a time period of about 10 to 30 min. Unfortunately, this assay can reveal only major differences in heat shock sensitivity. It has, however, been discovered that modifications introduced to this assay allow more precise quantitative evaluation of the differences in the survival rate. In the modified assay, cells are grown in a liquid medium into a stationary phase. The liquid medium can be water or some other growth medium, such as the commercially available Yeast Minimal Medium (See, e.g., Atlas, et al., *HANDBOOK OF MICROBIOLOGICAL MEDIA* (CRC Press, Ann Arbor, Mich. (1993)). Equal amounts of cells are added to tubes containing the liquid medium, preferably water. At the same time, portions of these suspensions are plated on the growth media to score the viability before the heat shock, i.e., to serve as controls. The tubes are then placed in a PCR machine or a water-bath at a temperature ranging between about 40° C. and about 60° C., more preferably at a temperature between 50° C. and 55° C., and heat shocked for a time period ranging from about 0.5 minute to about 20 minutes, more preferably for a time period from about 3 minutes to about 12 minutes. It will be readily apparent to those of skill in the art that the specific reaction conditions employed will depend upon the amount of cells in the suspension and upon how deep into the stationary phase the tested cells are.

The heat-treated cells are then cooled down to a temperature ranging from 0° C. to about 30° C., more preferably to about room temperature (20° C.), and plated on the growth media to score viability after the heat shock. The ratio of the number of survivors in the tested strain (e.g., a strain carrying deletions in AFC1 or RCE1 or alterations in the RAS2 C-terminus CAMQ sequence) to the number of survivors in the control strain (i.e., the strain which has no deletions or alterations) defines the level of suppression of heat shock sensitivity. At the same time, the strains with plasmids carrying the wild type RAS2 gene are also tested for heat shock sensitivity to determine if the introduced changes by themselves have any effect on the rate of survival.

In a variation of the above assay, all tested strains are transferred to a 96-well microtiter plate and serially diluted 5-fold 5 times. An aliquot (about 6 $\mu$l) from each well is placed on the growth media to determine the viability of the strain. The plate is placed in a water-bath at a temperature of about 50° C. to about 55° C. Aliquots are removed after 7 and 12 minutes of heat treatment. The heat shock sensitivity is scored by determining which of the lowest dilutions still has survivors.

An additional assay to measure RCE1 function in Ras processing was to test growth at semi-permissive conditions of cells contains the Ras temperature sensitive mutant. RCE1 mutants decreased the maximum permissive temperature for growth. In one of the experiments carried out, 2 ODs ($\sim 2 \times 10^7$ cells) of cells without the RAS2$^{val19}$ plasmid and 3.5 ODs of cells with the RAS2$^{val19}$ plasmid were placed in the first row of the plate. Each row thereafter represents a 5-fold dilution. Cells were incubated at a temperature of about 50° C. for about 7 minutes. Longer incubation times showed even more dramatic effects. Heat shock sensitivity was reduced 5-fold. The following assay was used to measure suppression. Strains were grown in YM+supplements for about 2.5 days to an OD of about 2.6×10$^6$. Cells from each strain (in duplicate) carrying the RAS2$^{val19}$ plasmid were resuspended in 1 ml of water. 50 $\mu$l of each of the suspension was plated for viability. The tubes were then incubated for about 10 min at a temperature of about 50° C. After being cooled down to about room temperature, 650 $\mu$l and 150 $\mu$l aliquots were plated on the growth media to score the rate of survival.

Example 3

Yeasts Strains Used in the Various Assays

A. Strains Used in Temperature Sensitivity Experiments

The strains used in the temperature sensitivity experiments were obtained by crossing the W303 MATα Δafc1, Δrce1 strain to W303 MATa ras1::HIS3, ras2–23$^{ts}$ (PHY 1150).

Analysis of the segregants from the cross yielded the following strains:

Wild type: W303, MATa, ras1::HIS3, ras2–23$^{ts}$, ade2, leu2, his3, trp1, ura3

Δafc1: W303, MATa, ras1::HIS3, ras2–23$^{ts}$, ade2, Δafc1::HIS3, leu2, his3, trp1, ura3

Δrce1: W303, MATa, ras1::HIS3, ras2–23$^{ts}$, ade2, Δrce1::TRP1, leu2, his3, trp1, ura3

Δafc1, Δrce1: W303, MATa, ras1::HIS3, ras2–23$^{ts}$, ade2, Δafc1::HIS3, Δrce1::TRP1, leu2, his3, trp1, ura3

B. Strains Used in Heat Shock Assays

All strains were derived from the common laboratory strain W303 (JRY2334). AFC1 was deleted by homologous recombination using the construct in which a part of the open reading frame (ORF) is replaces with the HIS3 gene. For a discussion regarding the use of homologous recombination, see, e.g., Scherer, S., et al., "Replacement of chromosome segments with altered DNA sequences constructed in vitro," Proc. Natl. Acad. Sci. USA, 76(10) :4951–5 (1979). RCE1 was deleted using homologous recombination using a PCR product in which the coding region of TRP1 gene is flanked by ~40 bp sequences homologous to the sequences just upstream and downstream of the ORF encoding the RCE1 gene.

A double deletion strain was obtained by crossing Δafc1 MATα strain to Δrce1 MATa strain, followed by dissection of the sporulated diploid and analysis of the segregants.

Genotypes:

Wild type: W303, MATa, leu2, his3, trp1, ura3

Δafc1: W303, MATa, Δafc1::HIS3, leu2, his3, trp1, ura3

Δrce1: W303, MATa, Δrce1::TRP1, leu2, his3, trp1, ura3

Δafc1, Δrce1: W303, MATa, Δafc1::HIS3, Δrce1::TRP1, leu2, his3, trp1, ura3

The RAS2$^{val19}$ allele was introduced in these strains on URA3 CEN plasmid. Control strains carried URA3 CEN plasmid with wild type RAS2 gene.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of identifying a compound which inhibits the proteolytic removal of an AAX tripeptide of a CAAX protein in a cell, comprising the stress of:

conatacting a test compound with a sample comprising a cell expressing a functional Afc1p or Rce1p polypeptide, but not both, from a corresponding Afc1p or Rce1p-encoding nucleic acid, wherein the polypeptide mediates the proteolytic removal of an AAX tripeptide from a prenylated CAAX protein, and wherein the nucleic acid hybridizes under highly stringent conditions to a polynucleotide consisting of SEQ ID NO:1 or 3, respectively, and wherein the highly stringent conditions comprise hybridization and wash conditions selected to be 5° C. lower than the thermal melting point (Tm) for said polynucleotide at a defined ionic strength and pH: and measuring activity or expression of the polypeptide expressed by the cell, wherein compound-dependent inhibition of the activity or expression indicates that the compound inhibits the proteolytic renoval of the AAX tripeptide, wherein the cell is selected from a prokaryotic cell and a yeast cell.

2. The method of claim 1 wherein the sample is a cell lystate.

3. The method of claim 1, wherein said cell is selected from the group consisting of an Δafc1 cell, a Δrce1 cell, and an Δafc1 and Δrce1 cell.

4. The method of claim 1 wherein the cell is a prokaryotic cell.

5. The method of claim 1 wherein the cell is a yeast cell.

6. The method of claim 1 wherein the Afc1p and Rce1polypeptides comprise SEQ ID NO:2 and 4, respectively.

7. The method of claim 1 wherein the cell is a yeast cell and the Afc1p and Rce1p polypeptides comprise SEQ ID NO:2 and 4, respectively.

8. The method of claim 1, wherein the cell is a yeast cell and the activity is measured by monitoring heat shock snesitivity of the cell.

9. The method of claim 1 wherein the cell is a yeast cell, the Afc1p and Rce1p polypeptides comprise SEQ ID NO:2 and 4, respectively, and the activity is measured by monitoring heat shock sensitivity of cell.

10. The method of claim 1 wherein expression is measured using an ELISA.

11. A method of identifying a compound which inhibits the proteolytic removal of an AAX tripeptide of a CAAX protein in a cell, comprising the steps of:

contacting a test compound with a sample comprising a recombinant cell comprising a vector nucleic acid and expressing a polypeptide encoded by the vector nucleic acid, the polypeptide selected from the group consisting of a functional Afc1p and a functional Rce1p polypeptide, wherein the polypeptide mediates the proteolytic removal of an AAX tripeptide from a prenylated CAAX protein, and wherein the vector nucleic acid hybridizes under highly stringent conditions to a polynucleotide consisting of SEQ ID NO:1 or 3, respectively, and wherein the highly stringent conditions comprise hybridization and wash conditions selected to be 5° C. lower than the thermal melting point (Tm) for said polynucleotide at a defined ionic strength and pH; and measuring activity or expression of the Afc1p or Rce1p expressed by the cell, wherein compound-dependent inhibition of the activity or expression indicates that the compound inhibits the proteolytic removal of the AAX tripeptide.

12. The method of claim 11, wherein the sample is a cell lysate.

13. The method of claim 11, wherein said cell is a yeast cell selected from the group consisting of an Δafc1 cell, a Δrce1 cell, and an Δafc1 and Δrec1 cell.

14. The method of claim 11, wherein the cell is a eukaryotic cell.

15. The method of claim 11 wherein the cell is a prokaryotic cell.

16. The method of claim 11 wherein the cell is a yeast cell.

17. The method of claim 11 wherein the Afc1p and Rce1p polypeptides comprise SEQ ID NO:2 and 4, respectively.

18. The method of claim 11 wherein the cell is a yeast cell and the Afc1p and Rce1p polypeptides comprise SEQ ID NO:2 and 4, respectively.

19. The method of claim 11, wherein the cell is a yeast cell and the activity is measured by monitoring heat shock sensitivity of the cell.

20. The method of claim 11 wherein the cell is a yeast cell, the Afc1p and Rce1p polypeptides comprise SEQ ID NO1 and 4, respectively, and the activity is measured by monitoring heat shock sensitivity of the cell.

21. The method of claim 11 wherein expression is measured using a ELISA.

22. A method of identifying a compound which inhibits Rce1p activity or Afc1p activity, comprising the steps of:

expressing a polynucleotide which encodes a functional Afc1p or Rce1p polypeptide and hybridizes under highly stringent conditions to a nucleic acid consisting of SEQ D NO:1 or 3, respectively, wherein said polypeptide mediates the proteolytic removal of an AAX tripeptide from a prenylated CAAX protein, and said highly stringent conditions comprise hybridization and wash conditions selected to be 5° C. lower than the thermal melting point (Tm) for said nucleic acid at a defined ionic strength and pH;

isolating the polypeptide;

contacting a test compound units a sample comprising the isolated polypeptide: and measuring an activity selected from the group consisting of Afc1p activity and Rce1p activity, wherein compound-dependent inhibition of the activity indicates that the compound inhibits Rce1p activity or Afc1p activity.

23. The method of claim 22 wherein the Afc1p and Rce1p and Rce1p polypeptides comprise SEQ ID NO:2 and 4, respectively.

* * * * *

UNITED STATES PATENT AND TRADEMARK OFFICE
CERTIFICATE OF CORRECTION

PATENT NO. : 6,391,574 B1
DATED : May 21, 2002
INVENTOR(S) : Rine et al.

It is certified that error appears in the above-identified patent and that said Letters Patent is hereby corrected as shown below:

Column 39,
Line 46, please replace "stress" with -- steps --.
Line 47, please replace "conatacting" with -- contacting --.
Line 63, please replace "renoval" with -- removal --.
Line 66, please replace "lystate" with -- lysate --.

Column 40,
Line 50, please replace "Rce1polypeptides" with -- Rce1p polypeptides --.
Line 57, please replace "snesitivity" with -- sensitivity --.

Column 42,
Line 5, replace "SEQ ID NO1" with -- SEQ ID NO:2 --.
Line 23, please replace "units" with -- with --.
Line 31, please delete "and Rce1p".

Signed and Sealed this

Fifth Day of November, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 1825 base pairs
    (B) TYPE: nucleic acid
    (C) STRANDEDNESS: unknown
    (D) TOPOLOGY: unknown (ii) MOLECULE TYPE: Genomic DNA (xi) SEQUENCE DESCRIPTION: SEQ ID NO:1:

```
ACCTACCTTT TTTTCTATCT TCAACAACGA AACGCCTTAC ACACACACAC ACATACATCT      60

ACATACATAC ATACAAATAT ACATATATGT AAACTTGTAT ATTCATTCCT ATTAACCAAA     120

AAGAGGCAAT TAAACTTTTC CCTCTTTTTC TACGTCATTT ACTCAAAAAC TCTAATTCCT     180

TCGTCTCTGT TCTGCCATTT TCTCCAGAAA AAAATCGACG GGAAATAAAA AAAAAAAGAC     240

AACGAACAAG AGAAAAAGTT CGCGAATTAT AAACCACTTC TATAATTAAC AGGAAAAGGA     300

AGGAAAAAAA AGGAGGAAAA GAAAACTGCA GGCCTTTATT CATGTTTGAT CTTAAGACGA     360

TTCTCGACCA TCCTAATATC CCGTGGAAAT TAATCATTTC TGGGTTCTCG ATTGCCCAAT     420

TTTCTTTCGA ATCTTACTTG ACGTACAGAC AGTACCAGAA GCTATCTGAA ACAAAGTTGC     480

CACCTGTGCT GGAAGACGAA ATTGATGATG AAACTTTTCA TAAATCAAGG AACTACTCCC     540

GGGCCAAGGC CAAGTTCTCC ATTTTCGGTG ACGTCTATAA CCTAGCCCAA AAGCTAGTTT     600

TCATCAAATA CGACCTCTTC CCTAAAATCT GGCACATGGC CGTTTCTTTA TTGAATGCAG     660

TCCTGCCAGT CAGATTTCAT ATGGTCTCCA CTGTCGCACA GAGTTTTATG CTTCTTGGGT     720

CTCTTATCCA GTTTGTCTAC CTTGGTTGAT TTGCCACTCT CTTACTATAG CCATTTTGTC     780

CTGGAAGAAA AATTTGGTTT CAATAAATTG ACCGTCCAAC TATGGATCAC CGATATGATC     840

AAGAGTCTGA CTTTGGCGTA TGCTATTGGT GGCCCAATCC TTTACCTGTT CCTTAAGATC     900

TTTGATAAAT TCCCTACTGA TTTCCTTTGG TACATTATGG TCTTCTTGTT CGTTGTCCAA     960

ATCTTAGCCA TGACAATCAT TCCAGTCTTC ATCATGCCCA TGTTTAATAA GTTCACTCCA    1020

TTGGAGGACG GTGAACTGAA AAAATCTATT GAAAGTTTGG CCGATAGAGT TGGGTTCCCT    1080

CTAGATAAGA TTTTTGTCAT TGACGGCTCA AAAAGATCTT CTCATTCAAA CGCATATTTC    1140

ACAGGTTTGC CATTCACCTC CAAGAGAATT GTTTTGTTCG ACACTTTAGT GAACAGTAAT    1200

TCTACTGATG AAATTACGGC TGTTTTGGCC CATGAAATCG GTCACTGGCA AAAAAACCAC    1260

ATCGTTAATA TGGTCATCTT TAGTCAATTG CACACCTTCC TCATTTTCTC CCTTTTCACC    1320

AGCATCTACA GAAATACATC ATTTTACAAC ACCTTCGGCT TTTTCTTAGA GAAGTCCACT    1380

GGCAGTTTTG TTGATCCCGT TATCACTAAG GAATTCCCCA TTATCATTGG ATTTATGTTA    1440

TTTAACGACT TATTAACTCC ACTCGAATGT GCCATGCAAT TCGTGATGAG TTTAATTTCC    1500

AGAACTCATG AATATCAAGC TGATGCTTAT GCTAAAAAAT TGGGCTACAA GCAAAATCTA    1560

TGTAGGGCTC TAATTGATCT ACAAATCAAA AACCTTTCCA CCATGAATGT AGATCCTCTG    1620

TATTCTAGCT ATCATTATTC CCATCCAACT CTAGCTGAAA GATCGACCGC TCTAGACTAT    1680

GTTAGTGAAA AGAAGAAAAA CTAATCTATA GAGTACACAT ATTAGCATGT ACCGTTAAAT    1740

TCAGCTTCGT TATGTCTATA TCTACATACA TACACAGGTA TCTACTATAA GAATAAAGGA    1800

AAGAAAAAAT AAACGATTAA ACATT                                          1825
```

(2) INFORMATION FOR SEQ ID NO:2:

(i) SEQUENCE CHARACTERISTICS:
        (A) LENGTH: 2850 base pairs
        (B) TYPE: nucleic acid
        (C) STRANDEDNESS: unknown (D) TOPOLOGY: unknown (ii) MOLECULE TYPE: Genomic DNA (xi) SEQUENCE DESCRIPTION: SEQ ID NO:2:

```
TGAACTGTTG ATGAACAAAG AGAAGCTGAC AAGCATCAAA GCTTTGTACG ATGATTTCCA    60
TTCAAAAATT TGTGAATATG AAACCAAGTT CAACAAGAAT TTTCTTGAAT TAAATGAGTT   120
ATATAATATG AATAGGGGAG ACCGTAGGCC AAAGGAACTG AAATTTACAG ATTTTATTAC   180
TTCACAGCTG TTTAACGATA TCGAAAGCAT TTGCAACTTG AAAGTTAGTG TTCACAACTT   240
ATCCAACATT TTTAAAAAAC AGGTCAGTAC CCTAAAACAA CACTCAAAGC ACGCATTATC   300
TGAGGATTCA ATATCGCACA CAGGTAACGG TAGTTCATCG TCGCCCAGTT CAGCGTCATT   360
AACGCCAGTA ACTTCTTCAT CCAAGAGTAG TTTATTTTTA CCTAGCGGTA GCTCGTCTAC   420
TTCCCTGAAA TTTACAGACC AGATTGTTCA TAAATGGGTT AGGATTGCTC CTTTACAGTA   480
CAAACGAGAC ATTAATGTGA ACTTGGAATT TAATAAGGAC ATTAAGGAAA CTTTAATTCC   540
AAGTTTTGAA AGCTGCCTAT GTTGTAGGTT TTATTGCGTT CGAGTAATGA TTAAATTTGA   600
AAACCATCTT GGCGTAGCGA AGATTGATAT CCCTATTTCT GTTAGGCAAG TGACAAAATA   660
AAAAAACATT AGAAAAAATT CTCGTTACTT TTCTTATAGA TATAGATATA TGTATGGTTT   720
GCTTATAGAT GAAGGTATTT ATCGCGTCCT TTGTATTCCC TATTATTAAT AAAATTCTTT   780
TAAAATGCAT TTTCTGGTGC TCTTTTGTTG CTTCTGTATT TTTTTTTTTT TGGACCACTG   840
GATGGAAAAC CTTTGATGAT TTTATTACCT TTATTTTAAC TTACTAAAAT ATCGAGATTT   900
CAGGAACAAA ACATAGAATT TTCTTTGTCA AGAAAAATAA AACGAAATAA ATTGATGCTT   960
TGACTACTGA CTGTCTGTCA TAGAGAGAAC CAGAACAGCA ATGCTACAAT TCTCAACATT  1020
TCTAGTGCTC CTATACATCT CCATATCCTA TGTGCTACCG CTATATGCAA CTTCACAACC  1080
AGAAGGGTCT AAACGAGATA ATCCTCGAAC GATTAAATCT CGCATGCAAA AACTTACAAT  1140
TATGCTAATT TCCAACCTTT TTTTGGTGCC TTTTTTACAA TCTCAATTAT CTAGTACCAC  1200
TTCACATATA AGTTTCAAGG ACGCATTTTT AGGCTTAGGT ATTATCCCAG GTTATTACGC  1260
TGCATTGCCA AACCCTTGGC AATTCAGCCA GTTCGTGAAA GACTTAACGA AATGTGTTGC  1320
GATGTTATTG ACCTTATATT GTGGACCCGT TTTAGATTTT GTATTATATC ATTTATTAAA  1380
TCCAAAGAGC TCTATACTTG AAGATTTTA CCATGAATTC CTGAATATTT GGAGTTTCAG  1440
GAATTTTATA TTTGCACCAA TAACTGAGGA AATATTTTAC ACGTCAATGC TTTTGACTAC  1500
GTACTTAAAC CTAATACCGC ATTCGCAACT AAGCTATCAA CAGTTATTTT GGCAACCATC  1560
GCTTTTTTTT GGACTTGCGC ACGCACACCA TGCTTATGAG CAATTACAGG AAGGCTCCAT  1620
GACAACTGTT TCCATTCTGC TGACAACATG CTTCCAAATT TTATACACAA CACTTTTTGG  1680
AGGGTTAACC AAGTTTGTAT TGCAATATCA TGGGGTTTAA TGGTCCTTCA AGATTGAATT  1740
TACATTTCAC AGTAGTAGAC AAGAAAGCTG GACGCATTTC CAAATTGGTC TCTCAATCTG  1800
GAATAAGTGC TACTTCGCAC TGCTGGTCCT TGGATTAATA TCCCTGAAGG ATACCTTACA  1860
AACTCTGGTA GGAACTCCTG GTTATAGAAT AACCCTTTAG CCTTTTTTAC GTACTTGTAT  1920
ACCGTTTAAA ATTTCCTATG TACTATAACC TTTTTTCACT ACTATTATGG AATTCTATCG  1980
AGCGACCGGG CTTTTGTTAC GGAAGAGTGA AAAAATCGAG TTTTGGTGTT TTGGTGAAAG  2040
AATTTGGAGG ACTATAAAGT ACCTATACTT TGTATTACGG ACTCAATAAC AAGTCGTTCG  2100
TGTCAGTGGT ATTGAAGTTG TCAGATCTAA GAGTAGAGAG AAGGTGGCAT CTAATAGGTT  2160
TCGACGTTTT TCTTTTTTTA AGGTTTTTAT TTGGTCTCCT AGAATTTAAG GTCTTAGTTA  2220
```

```
GTTTTGGTTT GTTTTGTGGG TTACATATTT TCAATTCAAA GGAGAATTTA GCTGTCTTTT   2280

ATAATGTCCA ATAGAGATAA CGAGAGCATG CTGCGTACTA CATCAAGCGA TAAGGCGATC   2340

GCTAGTCAAA GGGATAAACG GAAGTCTGAA GTTTTGATTG CTGCACAGTC CCTTGACAAT   2400

GAAATCCGCA GCGTAAAAAA CCTAAAAAGA TTGTCGATTG GGTCAATGGA TTTACTTATT   2460

GATCCAGAAT TAGATATAAA ATTCGGTGGG GAATCTAGTG GGAGACGATC ATGGTCTGGC   2520

ACGACATCCA GTTCTGCGTC AATGCCAAGT GACACAACCA CCGTTAATAA CACACGATAT   2580

AGCGATCCAA CTCCGCTAGA GAACTTGCAT GGGAGGGGTA ACTCAGGGAT AGAATCCTCC   2640

AATAAGACTA AAATTAAATG CTAACGTATT AAAGAAAAAC TTATTATGGG TTCCCGCCAA   2700

TCAACACCCT AACGTTAAGC CTGATAATTT CCTAGAGCTT GTACAAGATA CTTTACAAAA   2760

TATACAACTA AGCGACAATG GTGAAGATAA TGATGGGAAT AGCAATGAAA ATAACGATAT   2820

TGAGGATAAT GGGGAGGATA AAGAATCACA                                   2850
```

(2) INFORMATION FOR SEQ ID NO:3:

(i) SEQUENCE CHARACTERISTICS:
        (A) LENGTH: 451 amino acids
        (B) TYPE: amino acid
        (D) TOPOLOGY: unknown (ii) MOLECULE TYPE: peptide (ix) FEATURE:
        (A) NAME/KEY: peptide
        (B) LOCATION: 1...451
        (D) OTHER INFORMATION: /note = "The sequence of the Afc1p
            protein from yeast presented as a polypeptide sequence"

(xi) SEQUENCE DESCRIPTION: SEQ ID NO:3:

```
Met Phe Asp Leu Lys Thr Ile Leu Asp His Pro Asn Thr Pro Trp Lys
 1               5                  10                  15

Leu Ile Ile Ser Gly Phe Ser Ile Ala Gln Phe Ser Phe Glu Ser Tyr
            20                  25                  30

Leu Thr Tyr Arg Gln Tyr Gln Lys Leu Ser Glu Thr Lys Leu Pro Pro
        35                  40                  45

Val Leu Glu Asp Glu Ile Asp Asp Glu Thr Phe His Lys Ser Arg Asn
    50                  55                  60

Tyr Ser Arg Ala Lys Ala Lys Phe Ser Ile Phe Gly Asp Val Tyr Asn
65                  70                  75                  80

Leu Ala Gln Lys Leu Val Phe Ile Lys Tyr Asp Leu Phe Pro Lys Ile
                85                  90                  95

Trp His Met Ala Val Ser Leu Leu Asn Ala Val Leu Pro Val Arg Phe
            100                 105                 110

His Met Val Ser Thr Val Ala Gln Ser Leu Cys Phe Leu Gly Leu Leu
        115                 120                 125

Ser Ser Leu Ser Thr Leu Val Asp Leu Pro Leu Ser Tyr Tyr Ser His
    130                 135                 140

Phe Val Leu Glu Glu Lys Phe Gly Phe Asn Lys Leu Thr Val Gln Leu
145                 150                 155                 160

Trp Ile Thr Asp Met Ile Lys Ser Leu Thr Leu Ala Tyr Ala Ile Gly
                165                 170                 175

Gly Pro Ile Leu Tyr Leu Phe Leu Lys Ile Phe Asp Lys Phe Pro Thr
            180                 185                 190

Asp Phe Leu Trp Tyr Ile Met Val Phe Leu Phe Val Val Gln Ile Leu
        195                 200                 205
```

```
Ala Met Thr Ile Ile Pro Val Phe Ile Met Pro Met Phe Met Lys Phe
    210                 215                 220

Thr Pro Leu Glu Asp Gly Glu Leu Lys Lys Ser Ile Glu Ser Leu Ala
225                 230                 235                 240

Asp Arg Val Gly Phe Pro Leu Asp Lys Ile Phe Val Ile Asp Gly Ser
                245                 250                 255

Lys Arg Ser Ser His Ser Asn Ala Tyr Phe Thr Gly Leu Pro Phe Thr
                260                 265                 270

Ser Lys Arg Ile Val Leu Phe Asp Thr Leu Val Asn Ser Asn Ser Thr
            275                 280                 285

Asp Glu Ile Thr Ala Val Leu Ala His Glu Ile Gly His Trp Gln Lys
    290                 295                 300

Met His Ile Val Asn Met Val Ile Phe Ser Gln Leu His Thr Phe Leu
305                 310                 315                 320

Ile Phe Ser Leu Phe Thr Ser Ile Tyr Arg Asn Thr Ser Phe Tyr Asn
                325                 330                 335

Thr Phe Gly Phe Phe Leu Glu Lys Ser Thr Gly Ser Ser Phe Val Asp
                340                 345                 350

Pro Val Ile Thr Lys Glu Phe Pro Ile Ile Ile Gly Phe Met Leu Phe
                355                 360                 365

Asn Asp Leu Leu Thr Pro Leu Glu Cys Ala Met Gln Phe Val Met Ser
    370                 375                 380

Leu Ile Ser Arg Thr His Glu Tyr Gln Ala Asp Ala Tyr Ala Lys Lys
385                 390                 395                 400

Leu Gly Tyr Lys Gln Asn Leu Cys Arg Ala Leu Ile Asp Leu Gln Ile
                405                 410                 415

Lys Asn Leu Ser Thr Met Asn Val Asp Pro Leu Tyr Ser Ser Tyr His
                420                 425                 430

Tyr Ser His Pro Thr Leu Ala Glu Arg Leu Thr Ala Leu Asp Tyr Val
            435                 440                 445

Ser Glu Lys
    450

(2) INFORMATION FOR SEQ ID NO:4:

(i) SEQUENCE CHARACTERISTICS:
        (A) LENGTH: 315 amino acids
        (B) TYPE: amino acid
        (D) TOPOLOGY: unknown (ii) MOLECULE TYPE: peptide (ix) FEATURE:
        (A) NAME/KEY: peptide
        (B) LOCATION: 1...315
        (D) OTHER INFORMATION: /note = "The sequence of the Rcelp
            protein from yeast presented as a polypeptide sequence"

(xi) SEQUENCE DESCRIPTION: SEQ ID NO:4:

Met Leu Gln Phe Ser Thr Phe Leu Val Leu Leu Tyr Ile Ser Ile Ser
1               5                   10                  15

Tyr Val Leu Pro Leu Tyr Ala Thr Ser Gln Pro Glu Gln Ser Lys Arg
                20                  25                  30

Asp Asn Pro Arg Thr Ile Lys Ser Arg Met Gln Lys Leu Thr Ile Met
            35                  40                  45

Leu Ile Ser Asn Leu Phe Leu Val Pro Phe Leu Gln Ser Gln Leu Ser
    50                  55                  60
```

-continued

```
Ser Thr Thr Ser His Ile Gly Phe Lys Asp Ala Phe Leu Gly Leu Gly
 65                  70                  75                  80

Ile Ile Pro Gly Tyr Tyr Ala Ala Leu Pro Asn Pro Trp Gln Phe Ser
                 85                  90                  95

Gln Phe Val Lys Asp Leu Thr Lys Cys Val Ala Met Leu Leu Thr Leu
            100                 105                 110

Tyr Cys Gly Pro Val Leu Asp Phe Val Leu Tyr His Leu Leu Asn Pro
        115                 120                 125

Lys Ser Ser Ile Leu Glu Asp Phe Tyr His Glu Phe Leu Asn Ile Trp
        130                 135                 140

Ser Phe Arg Asn Phe Ile Phe Ala Pro Ile Thr Glu Glu Ile Phe Tyr
145                 150                 155                 160

Thr Ser Met Leu Leu Thr Thr Tyr Leu Asn Leu Ile Pro His Ser Gln
                165                 170                 175

Leu Ser Tyr Gln Gln Leu Phe Trp Gln Pro Ser Leu Phe Phe Gly Leu
                180                 185                 190

Ala His Ala His His Ala Tyr Glu Glu Leu Gln Glu Gly Ser Met Thr
            195                 200                 205

Thr Val Ser Ile Leu Leu Thr Thr Cys Phe Gln Ile Leu Tyr Thr Thr
        210                 215                 220

Leu Phe Gly Gly Leu Thr Lys Phe Val Phe Val Arg Thr Gly Gly Asn
225                 230                 235                 240

Leu Trp Cys Cys Ile Ile Leu His Ala Leu Cys Asn Ile Met Gly Phe
                245                 250                 255

Pro Gly Pro Ser Phe Leu Asn Leu His Phe Thr Val Val Asp Lys Lys
                260                 265                 270

Ala Gly Arg Ile Ser Lys Leu Val Ser Ile Trp Asn Lys Cys Tyr Phe
        275                 280                 285

Ala Leu Leu Val Leu Gly Leu Ile Ser Leu Lys Asp Thr Leu Gly Thr
        290                 295                 300

Leu Val Gly Thr Pro Gly Tyr Arg Ile Thr Leu
305                 310                 315
```